US009179855B2

(12) United States Patent
Burdea et al.

(10) Patent No.: US 9,179,855 B2
(45) Date of Patent: Nov. 10, 2015

(54) SYSTEM AND METHOD FOR PAIN REDUCTION

(75) Inventors: Grigore C. Burdea, Highland Park, NJ (US); Bryan A. Rabin, Somerset, NJ (US)

(73) Assignee: Bright Cloud International Corp., Highland Park, NJ (US)

( * ) Notice: Subject to any disclaimer, the term of this patent is extended or adjusted under 35 U.S.C. 154(b) by 625 days.

(21) Appl. No.: 13/285,987

(22) Filed: Oct. 31, 2011

(65) Prior Publication Data

US 2012/0136274 A1    May 31, 2012

Related U.S. Application Data

(60) Provisional application No. 61/408,670, filed on Nov. 1, 2010.

(51) Int. Cl.
| | |
|---|---|
| *A61B 5/04* | (2006.01) |
| *A61B 5/0484* | (2006.01) |
| *A61B 5/11* | (2006.01) |
| *A61B 5/00* | (2006.01) |
| *A63F 13/20* | (2014.01) |
| *A63F 13/40* | (2014.01) |
| *A63B 22/20* | (2006.01) |
| *A63B 24/00* | (2006.01) |
| *A61B 5/021* | (2006.01) |
| *A61B 5/024* | (2006.01) |
| *A61B 5/053* | (2006.01) |
| *A61B 5/16* | (2006.01) |
| *A63B 23/035* | (2006.01) |
| *A63B 23/12* | (2006.01) |
| *A63B 71/00* | (2006.01) |
| *A63B 71/06* | (2006.01) |

(52) U.S. Cl.
CPC ......... *A61B 5/04842* (2013.01); *A61B 5/04845* (2013.01); *A61B 5/04847* (2013.01); *A61B 5/1104* (2013.01); *A61B 5/4824* (2013.01); *A63B 22/20* (2013.01); *A63B 24/0087* (2013.01); *A63F 13/06* (2013.01); *A63F 13/10* (2013.01); *A61B 5/021* (2013.01); *A61B 5/024* (2013.01); *A61B 5/0531* (2013.01); *A61B 5/165* (2013.01); *A63B 23/03508* (2013.01); *A63B 23/03541* (2013.01); *A63B 23/1209* (2013.01); *A63B 2024/0093* (2013.01); *A63B 2024/0096* (2013.01); *A63B 2071/0072* (2013.01); *A63B 2071/0638* (2013.01); *A63B 2071/0658* (2013.01); *A63B 2220/13* (2013.01); *A63B 2220/51* (2013.01); *A63B 2220/70* (2013.01); *A63B 2220/72* (2013.01); *A63B 2220/76* (2013.01); *A63B 2220/806* (2013.01); *A63B 2225/20* (2013.01); *A63B 2225/50* (2013.01); *A63B 2230/062* (2013.01); *A63B 2230/105* (2013.01); *A63B 2230/425* (2013.01); *A63B 2230/505* (2013.01); *A63B 2230/655* (2013.01); *A63F 2300/1012* (2013.01); *A63F 2300/6027* (2013.01); *A63F 2300/6045* (2013.01); *A63F 2300/8094* (2013.01)

(58) Field of Classification Search
CPC .. A61B 5/0482; A61B 5/0476; A61B 5/4824; A61B 5/486; A63F 13/10; A63F 13/12; A63F 13/06; A63F 13/6045
USPC .............................. 600/544, 545; 463/30, 36
See application file for complete search history.

(56) References Cited

U.S. PATENT DOCUMENTS

| | | | | |
|---|---|---|---|---|
| 5,377,100 | A * | 12/1994 | Pope et al. | 600/545 |
| 7,892,178 | B1 * | 2/2011 | Bady et al. | 600/500 |
| 2009/0131225 | A1 * | 5/2009 | Burdea et al. | 482/5 |

*Primary Examiner* — Etsub Berhanu
(74) *Attorney, Agent, or Firm* — Graham Curtin (57) ABSTRACT

Systems and methods for treating pain are described. Systems and methods for treating pain using video games, tilt tables and bio-sensors are described wherein the level of the video game is controlled by a computer based on the feedback from a patient. Corresponding systems are also disclosed.

2 Claims, 8 Drawing Sheets

SYSTEM AND METHOD FOR PAIN REDUCTION

This application claims the benefit of U.S. Provisional Application No. 61/408,670, filed Nov. 1, 2010, which is incorporated by herein by reference.

BACKGROUND

Several patient groups suffer from pain which can be acute or chronic. Patients with acute pain are those who suffered burns that need to be dressed, or those who have had recent surgery (such as implant for shoulder or hip). Other patients with chronic pain are those post-traumatic brain injury, or with cancer, or with arthritis. If chronic pain is not treated it can lead to depression and worsening of overall health.

Several approaches exist to mitigating pain. Traditional approaches are medication (opioids such a morphine) or psychological coaching. Virtual reality has been used recently to treat pain by providing a distraction. If the pain sensation is not perceived because the centers in the brain are distracted, then the effect of pain is diminished.

Figure 1:
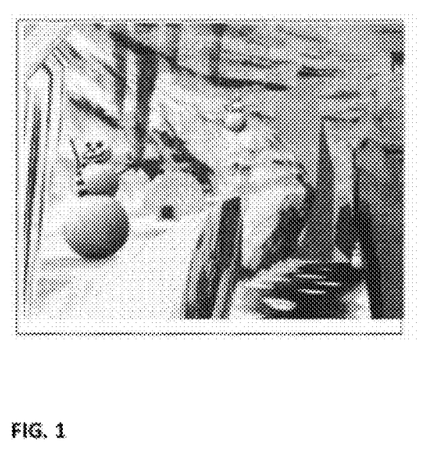
FIG. 1 illustrates a Virtual Reality scene from "Snow-World" therapeutic game (Hunter Hoffman).

Virtual reality to treat pain has been used in the form of specially-designed games, which are presented to the patients in stereo on head-mounted displays. In the case of the "SnowWorld" system developed by Hunter Hoffman (U. Washington) for alleviating pain during burn dressing, the scene is "cold" through the use of shades of blue and depiction of snow and snowmen. This, together with a pleasant music the patient hears, is designed to "cool" and calm the patient. Virtual reality for arthritic pain was designed to "warm" the patient, so shades of red were used. FIG. 1 illustrates a Virtual Reality scene from "SnowWorld" therapeutic game (Hunter Hoffman).

The degree of pain (pain index) the patient feels has been traditionally measured through pencil-and paper methods (subjective questionnaires), and more recently through bio-measures (skin sweat, pulse, respiration rhythm or volume).

SUMMARY OF THE INVENTION

In accordance with an aspect of the present invention, methods and systems are provided to treat a patient's pain.

In accordance with one method of the present invention, EEG data is sensed with a neuroheadset before beginning a treatment routine and inputting the EEG data into a computer, the computer processes the EEG data to establishing a baseline parameter of the EEG data for the patient, the computer shows a plurality of therapeutic videogames to the patient so that the patient performs physical and cognitive activities in accordance with the therapeutic videogame, a system continues to sense EEG data with the neuroheadset while the patient performs activities in accordance with the therapeutic videogame to determine a measured parameter of the EEG data while the patient performs activities, wherein the computer causes the video to vary the type, difficulty and duration of the physical and cognitive activities the patient is to perform when the measured parameter of the EEG data varies from the baseline parameter of the EEG.

The computer can cause the therapeutic videogame to vary the type, difficulty and duration of the physical and cognitive activities the patient is to perform when the measured parameter of the EEG data diverges more than a threshold from the baseline parameter.

In accordance with an aspect of the invention, the measured parameter indicates a level of pain and stress the patent is under while performing the physical and cognitive activities required by the therapeutic game play, while the patient's arms are supported by the rehabilitation table.

In accordance with a further aspect, when the EEG data is less than a baseline-determined threshold, the computer causes the therapeutic videogame to become less intense and demanding (less stressful) so that the patient is directed to perform less energetic physical activities, less difficult cognitive problems, or to rest, and thus reduce the amount of perceived pain and stress.

In accordance with another aspect of the present invention, when the measured parameter of the EEG data is greater than the baseline parameter plus the threshold, the computer causes the videogame to become more difficult (more stressful) so that the patient is directed to perform more energetic physical activities with the arms and hands or more difficult cognitive ones.

The parameter can be selected from the group consisting of: a frequency of the EEG data and the average amplitude of a band of frequencies in the EEG data, as measured by the neural headset.

Systems such as the ones disclosed herein to treat pain are also provided.

In accordance with one aspect of the present invention, a system for treating pain includes a computer, a rehabilitation table that can be tilted and lifted/lowered under control of the computer, a display that can display to the patient a plurality of videogames under control of the computer, the videogames having a physical and cognitive difficulty level associated with the movements shown in the videogame, one or more bio-sensors worn by the patient and connected to the computer to provide one or more inputs to the computer, wherein the computer analyzes the one or more inputs to the computer from the one or more bio-sensors and controls the difficulty level associated with the physical movements and cognitive problems shown in the videogame in accordance with the inputs. The system can also include a smell generator connected to the computer wherein the computer can selectively and interactively cause one of a plurality of odors to be generated near the patient, in response to events occurring in the therapeutic videogame; a plurality of smells that can excite or relax the patient, as needed (determined by input from the neural headset or from other bio-sensors).

The system can also include a 3D sound system connected to the computer wherein the computer can selectively cause one of a plurality of directional sounds to be generated near the patient in response to the events happening in the therapeutic videogame; computer alters intensity of sound, as well as type of sound and pitch in response to input from the neural headset and bio-sensors.

The system can also include a temperature control system connected to the computer wherein the computer can selectively cause the patient to sense varying temperatures, so to immerse the patients into the simulation and to reduce the level of stress and pain based on input from the neural headset.

The system can also include an input to the computer that indicates the medications the patient is taking and the computer receiving input from remote clinicians to alter the level/type of medication based on perceived level of pain.

The system can also include a camera or cameras connected to the computer that measures patient arm position on the therapeutic table, and the computer that uses these data together with grasp data sensed by a forearm support to project patient avatar actions in the therapeutic videogame.

The system can also include a movable forearm support under the patient's arm and that is connected to the computer to indicate a position of the patient's arm on the tilt table.

The system can also include a neuroheadset to be worn by the patient, the neuroheadset connected to the computer to provide EEG data to the computer. The neuroheadset can be controlled in the manner described above.

The system can also include a multitude of bio-sensors connected to same computer and used to alter game difficulty, table tilt, sound intensity and pitch, type of smells, temperature felt by patients.

The system can also include one or a multitude of patients, playing therapeutic games with the computer or against each other through a remote clinical server and the Internet.

The system can also include means by which computer can alter the tilting of the rehabilitation table so to reduce or increase the patient's level of distress/pain based on input from neural headset and other bio-sensors worn by patient.

DESCRIPTION

A virtual reality rehabilitation system for the shoulder, arm and hand which is subject of the patent application has been previously developed by one of the inventors of the present application. That system is described in with the United States Patent Office application Ser. No. 12/192,818, entitled "Rehabilitation Systems and Methods," filed on Aug. 15, 2008. This patent application is incorporated herein by reference as if fully set forth herein. The system in the above application includes:

(1) a tilting low-friction table with infrared LED at corners, made of wood; the table has a curved surface facing the patient.

(2) a low-friction forearm support with infrared LEDs, pressure sensor, surface contact detection, battery, electronics with ON/OFF switch, and a wireless transmitter. The top of the support has memory foam for comfort, Velcro strips for attachment to the forearm, and a rubber pear grasped by the patient. The bottom has Teflon beads for reduced friction.

(3) a shoulder assembly is worn on the opposite shoulder to the arm being rehabilitated. It consists of an infrared LED, a battery, a on/off switch, and Velcro strips for attachment.

(4) an overhead camera with infrared filter, part of the vision tracking system which measures arm movement on the table and shoulder leaning.

(5) a PC (preferably multi-core) that has wireless communication with the forearm support. With this information it updates the rehabilitation simulation it is running, and sends the graphics output to a large display facing the patient. This display can be a large high-density non-stereo TV.

(6) Internet communication allows game data to be uploaded on a clinical server to allow remote viewing by a clinician.

Figure 2:
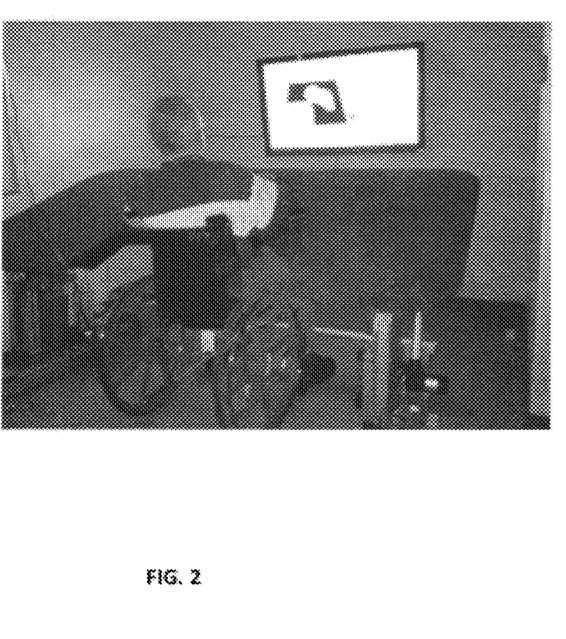
FIG. 2 illustrates a prototype BrightArm™ tilt table system (Bright Cloud International Corp) that can be used in accordance with various aspects of the present invention.

The tilt table, display and arm controller are illustrated in FIG. 2. It is capable of single arm and dual-arm rehabilitation in virtual environments. When dual arm rehabilitation is desired, two arm controllers are provided. A computer causes a therapeutic videogame to be displayed to a patient undergoing rehabilitation. The patient attempts to perform activities in accordance with the videogame being displayed. For example, the therapeutic videogame may show an object being moved across the table and the patient attempts to move an object (or just the arm) across the tilting table. Unlike prior art when the trained limb (arm or leg) is moved passively by the therapist, in our embodiment, the arm is moved actively bay the patient. It is appreciated that even with small movements of the arm the patient can play the therapeutic videogame.

The present system uses and builds on the above system. In accordance with one aspect of the present system and method, its use is extended from rehabilitation to the provision of pain relief, or the simultaneous provision of pain relief during rehabilitation. It is also envisioned that the system has the ability to let patients win the games, for example, by calibrating games to their abilities, automatically. The present system and methods also addresses the psychological/depression co-morbidity associated with chronic pain, by letting patients win and improving morale.

Figure 3A:
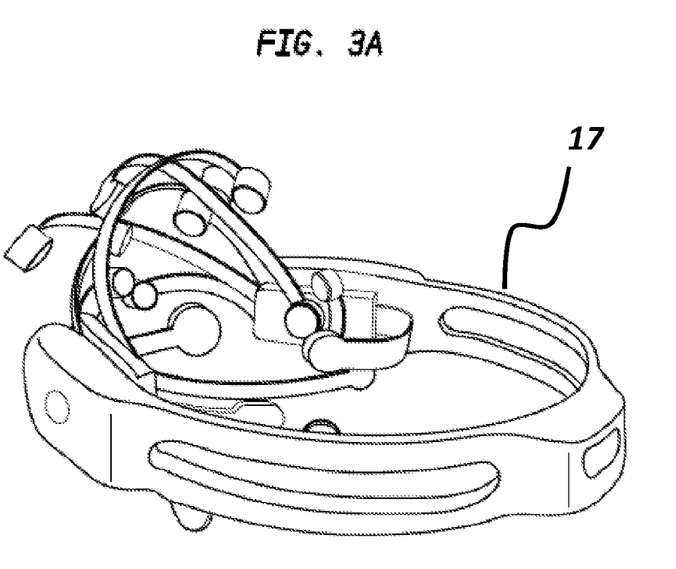
FIGS. 3a and 3b illustrate neuro-headsets that can be used in accordance with various aspects of the present invention.

In the present invention it is further envisioned that the traditional (paper and pencil) way of assessing pain will be supplemented through the use of a neuro-headset, which measures brain EEG signals. Such a headset is available commercially from Emotiv Systems Inc. (San Francisco, Calif.) and is shown in FIG. 3a.

Figure 3B:
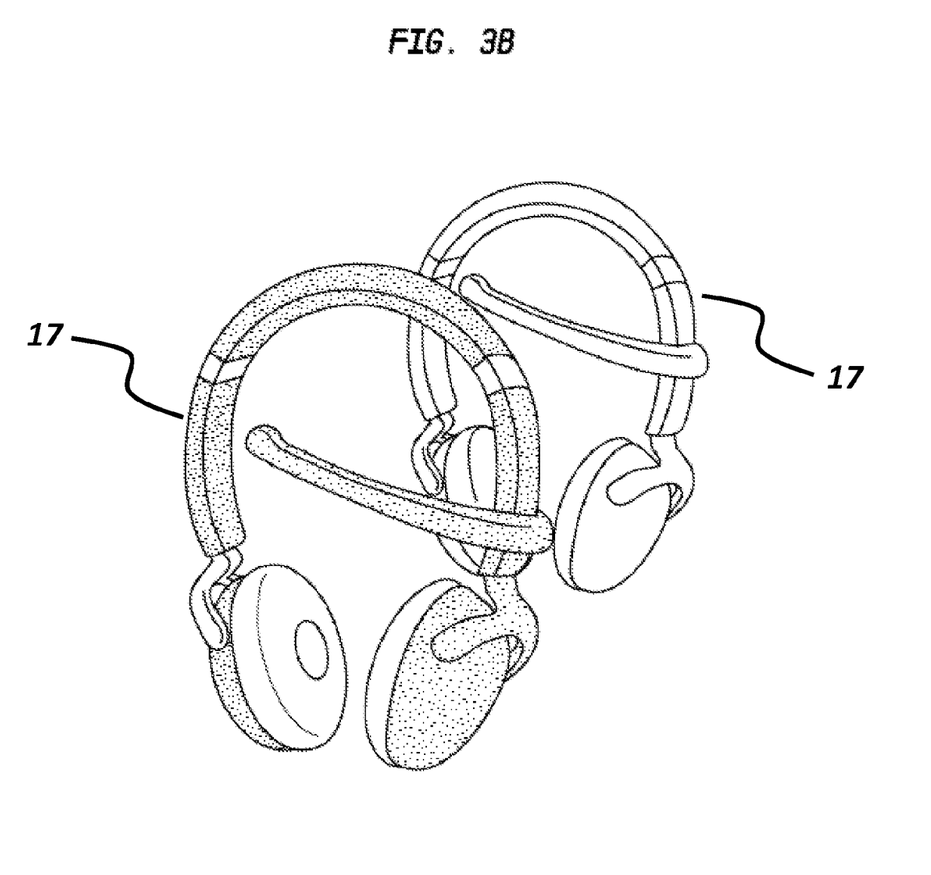

Another neural headset that can be used, also available commercially, is the NeuroSky MindSet (NeuroSky Co) shown in FIG. 3b. This neural interface can measure frontal lobe activity and transmit data to the computer. The MindSet is an easy to don simplified EEG device, with one dry electrode on the forehead and three on the earlobe. The EEG channel reading detects frequencies from 0 to 30 Hz and provides quantified "eSense" time-stamped readings of attention, ranging from 0 to 100. The 40-60 Hz range corresponds to average levels, with lower values indicating below average attention levels.

Figure 4:
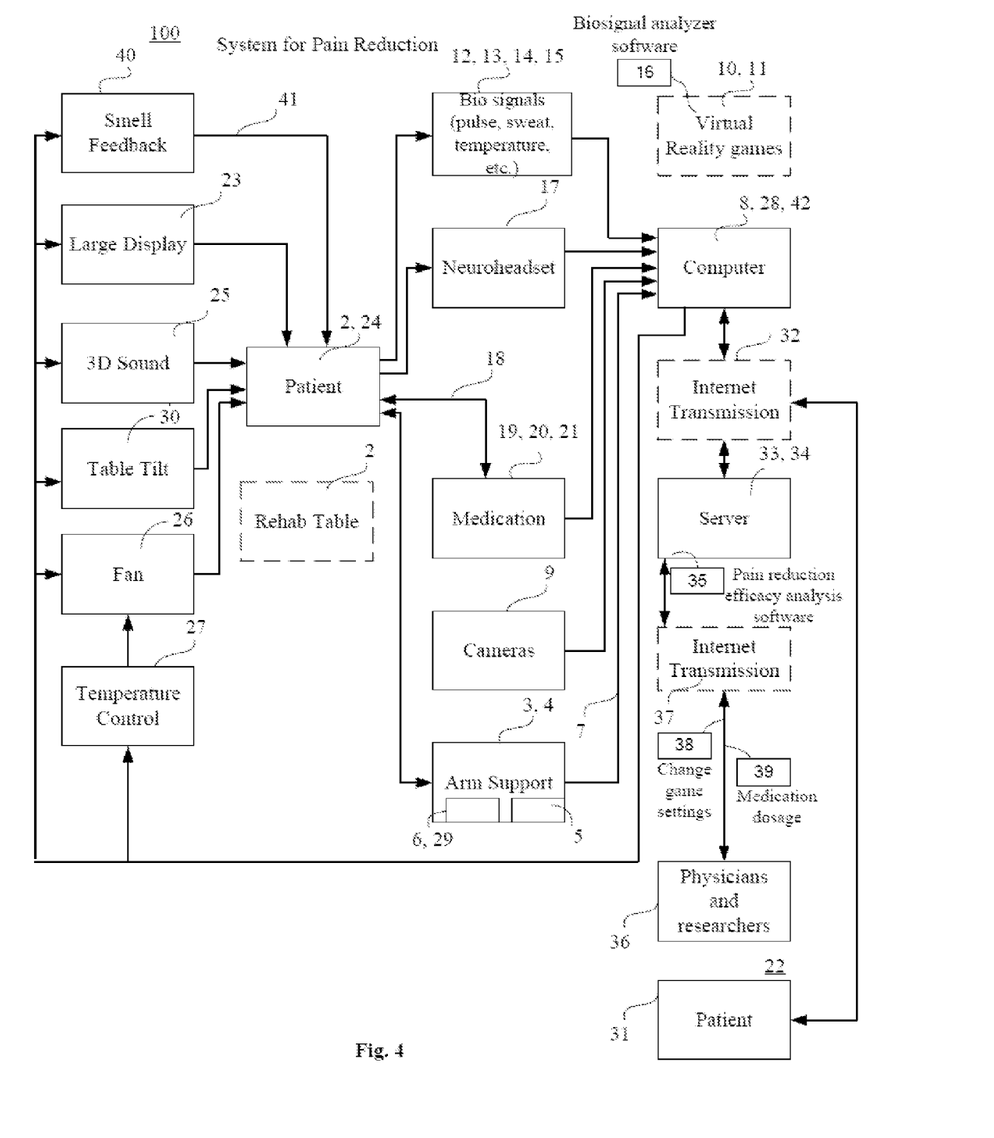
FIG. 4 illustrates a system used for pain reduction in accordance with an aspect of the present invention.

A system 100 in accordance with aspects of the present invention is shown in FIG. 4. A method 101 in accordance with aspects of the present invention is shown in FIG. 5.

Figure 5:
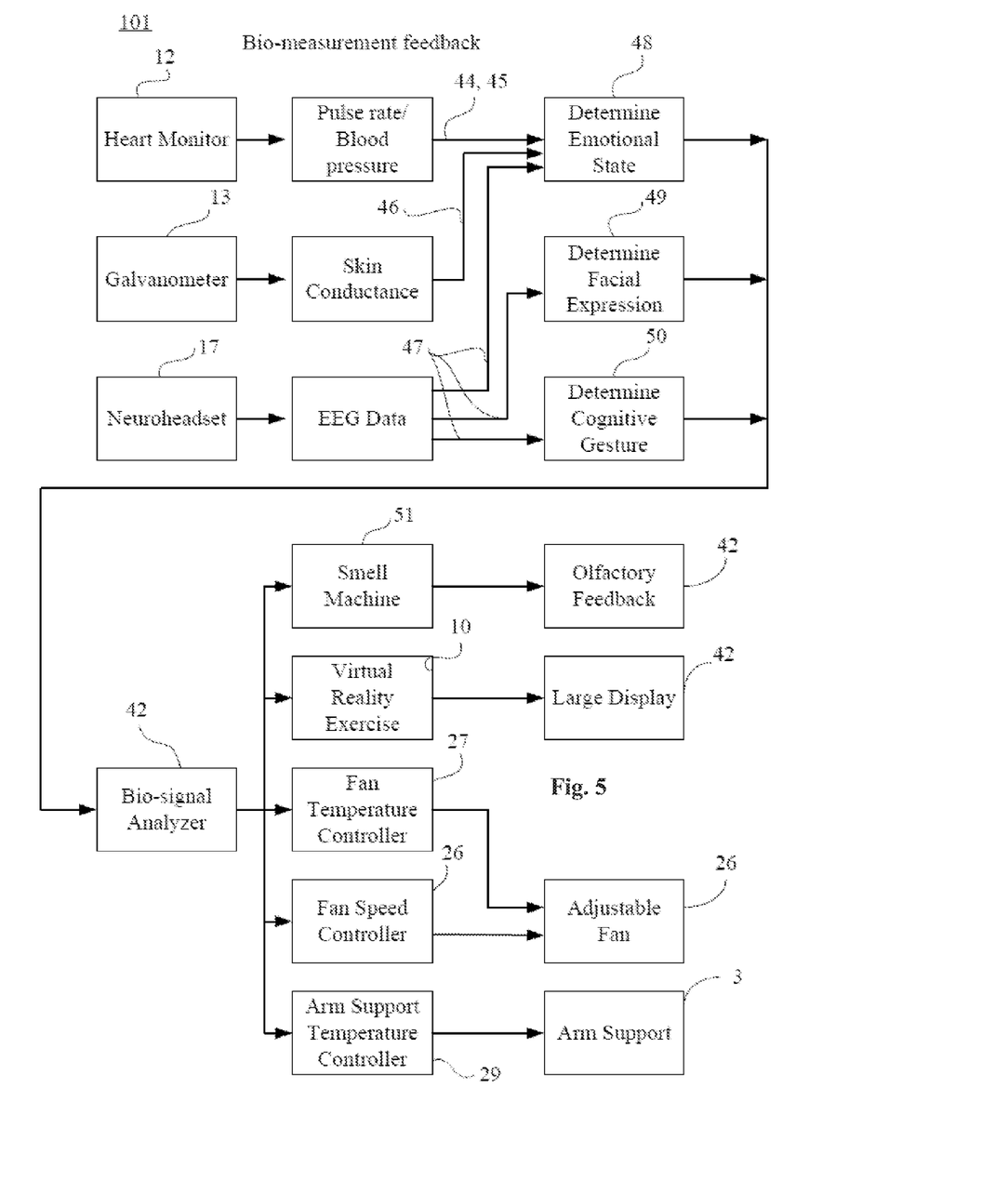
FIG. 5 illustrates a method used for pain reduction in accordance with an aspect of the present invention.

Referring to FIGS. 4 and 5, a patient 1 sits at special tilting rehabilitation table 2 with forearm 3 placed in forearm support 4. Forearm support 4 has electronic means for measuring patient 1 grasping strength 5 and temperature feedback plate 6. Forearm support further has communication means 7 to transmit and receive information from simulation computer 8. Overhead cameras 9 also transmit information to simulation computer 8 about the forearm 3 movement on table 2. It is envisioned that information from cameras 9 and forearm support communication means 7 is used by computer 8 to update a plurality of virtual reality games 10 which patient 1 plays. It is appreciated that computer 8 can be a PC, a laptop, tablet, and other similar equipment, as available commercially. A plurality of such games 10 form a library of games 11 to allow variation of the games 10 played.

While patient 1 plays games 10, his/her bio-signals of skin resistance, sweat 12, pulse 13, skin temperature 14, breathing rhythm 15 are sent to computer 8 which also runs bio-signal analyzer software 16. Patient 1 wears neuroheadset 17 which measures brain waves 18. It is appreciated that neuroheadset 17 can be one of those commercially available from Emotiv Systems Inc, NeuroSky Co and others. The use of the provided software development kit will allow the neuroheadset 17 to interface with the bio-signal analyzer software 41 running on computer 8. Medication dispenser 19 is further connected to computer 8 providing information on the type of medication 20 and medication intake information 21 the patient 1 is taking. Games 10 provide multi-modal feedback to patient 1. Graphics is presented to patient 1 on large display 23 which can be monoscopic or stereoscopic. For stereoscopic viewing patient 1 will wear stereo glasses 24 which provide increased immersion. Further feedback from games 10 is in the form of sound played by a 3D sound system 25. A fan 26 placed in close proximity to patient 1 blows air in response to game 10. Depending on the action in the game 10, a temperature control block 27 regulates the temperature of the air blown to the patient 1. Temperature control software 28 running on the computer 8 controls the temperature control block 27, as well as the temperature feedback block 6 in the forearm support 4. In a preferred embodiment temperature feedback block 6 is electronic. Its top surface 29 is in contact with the underside of the patient's forearm 3. Computer 8 also controls the table tilt block 30 such that patient 1 plays videogames 8 against different tilt angles of table 2. It is appreciated that to increase game difficulty table 2 is tilted upwards more. Table 2 height can also be controlled to ensure patient comfort. This is disclosed in U.S. patent application Ser. No. 13/026,197, also by one of the inventors, which is incorporated herein by reference.

In the above embodiment patient 1 can play with one forearm 3 or with both forearms. It is further envisioned that other patients 31 can play on similar systems, and they can play against each other.

In the present embodiment patient 1 needs to be active in the process of physical therapy, by moving the arms against the tilted table and by grasping the forearm support rubber grasp element 5. In this way it is envisioned that the physical exercise level exerted by patient 1 is substantially more that that required when playing by pressing a key on a keyboard, or by moving a mouse or a joystick (as previously done in SnowWorld game).

It is believed that the combination of physical exercise and distracting video games result in increased blood flow and muscle strength. Better blood circulation in the limbs and more muscle in turn can results in reduced pain.

Repetitive arm movements, as required during game play 10, since supported by the table 2 in the system 100, may better meet the need for active physical exercise in pain management, and are currently lacking in conventional treatment.

Repetitive arm movement, whether during uni-manual or bimanual games 10, will in turn induce neural changes in the brain of patient 1. It is envisioned that these neural changes will in turn benefit patients with chronic pain. An indirect measure of neural changes will be the change in baseline levels of the EEG signal 47 measured by neuro-headset 17.

Another feature of the present invention is the multimodality of interaction, such that patient 1 receives feedback from game 10 in the form of images projected on the large display 23, smell feedback 40, 3D sound 25, gravity loading through table tilt 30, varying wind temperature through fan 26 and temperature feedback through the forearm support temperature feedback 6.

Communication from each patient 1, and 31 is mediated by internet transmission 32 to a remote server 33. Such server 33 runs database 34 and pain reduction efficacy analysis software 35. Remote clinicians 36 log into server 33 through internet transmission 37. Based on pain reduction efficacy analysis 35 and database 34 they can change videogame 10 settings 38, and can change medication dosage 39. An olfactory machine 40 provides smell feedback 41 generated in response to commands from computer 8. Computer 8 gives olfactory commands in relation to the computer games 10.

The method 101 for pain reduction in virtual reality is described by the block diagram in FIG. 5.

The bio-signal analyzer 42 takes inputs from the neuroheadset 17, a heart rate monitor 12, and skin conductance monitor 13 to quantify the patient's 1 stress level 43. The neuroheadset 17 also allows for measurement of cognitive gestures 50 and facial expressions 49. The exercises 10 will adapt by modifying the difficulty, speed, graphics, colors, sounds, and sound volume in response to the output of the bio-signal analyzer 42. This will be done to minimize the patient's 1 pain and stress levels 43.

For NeuroSky use, if low attention levels are detected, due to patient distress, then more frequent cognitive cues will be presented, to draw attention to the exercises. Focusing baseline will be done on the MindSet, when patients will react to images on the display seen passively, without manual action. It is envisioned that these measures can be used as an additional input into the games, with the computer 8 controlling the system by automatically changing game 10 difficulty when a patient 1 loses focus for an extended time due to plain. Following the baseline, patients 1 will play a combination of uni- and bi-manual games 10, to improve executive function, focusing, short term visual, spatial and auditory memory, strengthening, and improved motor control.

A visual representation of relative stress level will be presented in the exercises 10 to provide patient 1 with biofeedback. Patient 1 will also be able to control the exercises 10 through the use of cognitive gestures 50, in addition to use of the forearm support 4 and grip reader 5. The bio-signal analyzer 42 will also determine whether to modify the fan 26 speed, fan temperature control 27, forearm support temperature 29 and smell feedback 52 based on the current inputs.

Stress Parameter

In one embodiment of the present invention a stress parameter is determined from an EGG signal taken from a game player, who may be a patient. A level of stress, which may be one of several levels of stress, or a binary level of stress (acceptable vs. too much stress) is associated with a level in an exercise game.

It is assumed that a patient 1, before or at starting an exercise 10 is at a baseline level of stress. This level of stress is associated with an EGG signal or a part of an EGG signal determined from the patient 1 with the neuro-headset 17 prior to engaging with the game 10. In a further embodiment of the present invention a baseline parameter is derived from an EGG signal 47 taken during a certain period.

It is known that an EGG signal 47 taken through a sensor or a plurality of signals taken through a plurality of sensors, for instance as part of a neuro-headset 17, can be characterized by several signal properties, including by not limited to: frequency, frequency band, amplitude, spectrum and statistical properties of frequency and amplitude of signals.

In one embodiment of the present invention an EGG signal 47 is characterized by an average amplitude of the EGG signal at a certain frequency. In one embodiment of the present invention the frequency is between 20 Hz and 70 Hz. In another embodiment of the present invention the frequency is between 30 Hz and 60 Hz. In one embodiment of the present invention the frequency is substantially 60 Hz.

In one embodiment of the present invention the EGG signal 47 is processed to determine an amplitude of the EGG signal 47 over a frequency of between 20-70 Hz. In one embodiment of the present invention the EGG signal 47 is processed to determine an amplitude of the EGG signal over a frequency of between 30-60 Hz. In one embodiment of the present invention the EGG signal is processed to determine an amplitude of the EGG signal over a frequency band around 60 Hz. In one embodiment of the present invention the signal over a preferred bandwidth is averaged and/or smoothed.

In one embodiment of the present invention an EGG signal component is extracted that has a stable baseline value and that changes measurably when a patient 1 playing the game 10 experiences stress or pain. For instance, a frequency component in a baseline value of a player's EGG has a first value prior to engaging with the game. When the player experiences increased pain or stress during playing the game, the frequency component in the EGG may go down measurably.

Accordingly, a stress parameter for the patient or player derived from the EGG signal can be determined by the computer 8. In accordance with an embodiment of the present invention a baseline stress parameter is determined from the EGG signal of the player or patient at a first moment or during a first period, which may be prior to playing a game 10, but can also be at any other moment during a game 10, for instance after completing a certain exercise or after reaching a certain defined level of accomplishment. A second stress parameter is determined from the EGG signal of the player or patient at a second moment or period following the first moment or period.

In one embodiment of the present invention, an exercise game 10 is designed that is associated with different levels of complexity and/or involvement of a patient 1. In one embodiment of the present invention a level of a game is associated with a measure of potential pain related to an injury, so that some game levels are more painful or stressful than others.

When the measured stress parameter derived from the patient's 1 EGG signal 47 by the computer 8 passes a certain threshold, the computer 8 decides that the game level is too stressful for the patient. In response, the computer changes the level of the game to a level that is less stressful. The computer can diminish the levels or stop the game completely to have the player rest and reach a measured stress level that is less than the measured stress level.

Figure 6:
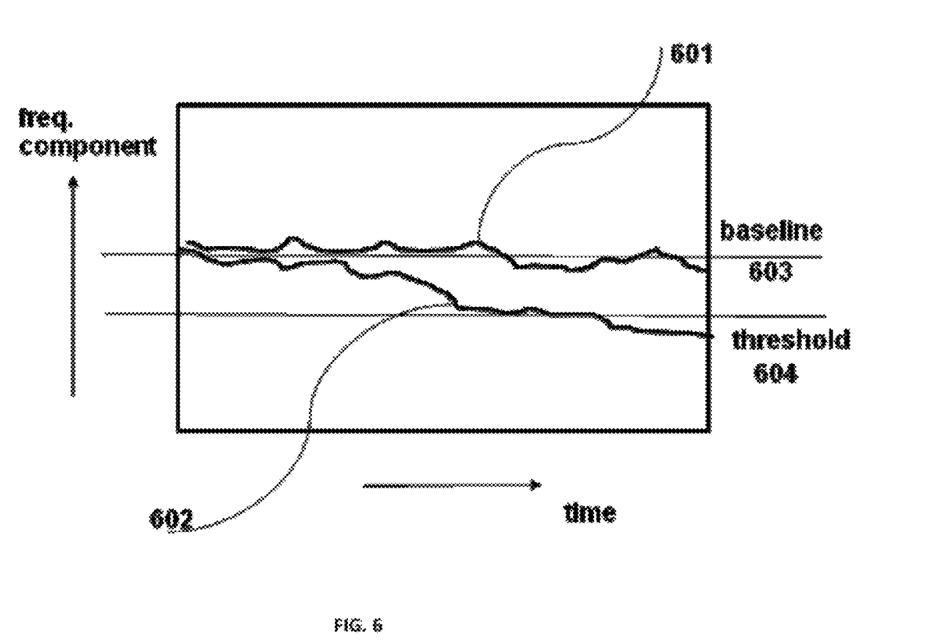
FIGS. 6 and 7 illustrate the processing of EEG data in accordance with an aspect of the present invention.

This is illustrated in FIG. 6. An EGG signal is measured over a period of time and a smoothed amplitude of a frequency component, for instance over a certain bandwidth of the EGG frequency band, is determined and is shown as curve 601. The computer 8 derives an average value 603, which serves in this illustrative example as a baseline stress parameter. During game play the smoothed amplitude over the same bandwidth as the baseline parameter is determined as a curve 602. A threshold 604 determines a level of acceptability of stress. This threshold can be predetermined or can be determined empirically during play and thus can be adjusted. When the curve 602 passes the threshold 604 an unacceptable stress ||baseline-threshold|| is reached. The bio-signal analyzer software 41 running on computer 8, based on passing the threshold, decides to ease on the level of complexity, for instance by adjusting the tilt of the rehabilitation table 2 through the table tilt bloc 30.

The computer 8 is programmed with additional tools. For instance a simple slope analysis shows that the stress level of the patient 1 deteriorates with time. The computer 8, based on this analysis, may change the guidance of the computer game, for instance by slowing a pace or by resetting some of the limits of the required movements. The computer game 10 is thus part of a feedback loop that ensures that the patient 1 remains in an acceptable level of stress or pain.

In one embodiment of the present invention the stress parameter decreases in value when the stress and pain levels go up. In another embodiment of the present invention a parameter is determined from the EGG signal 47 that increases in value when the stress and pain level go up.

Figure 7:
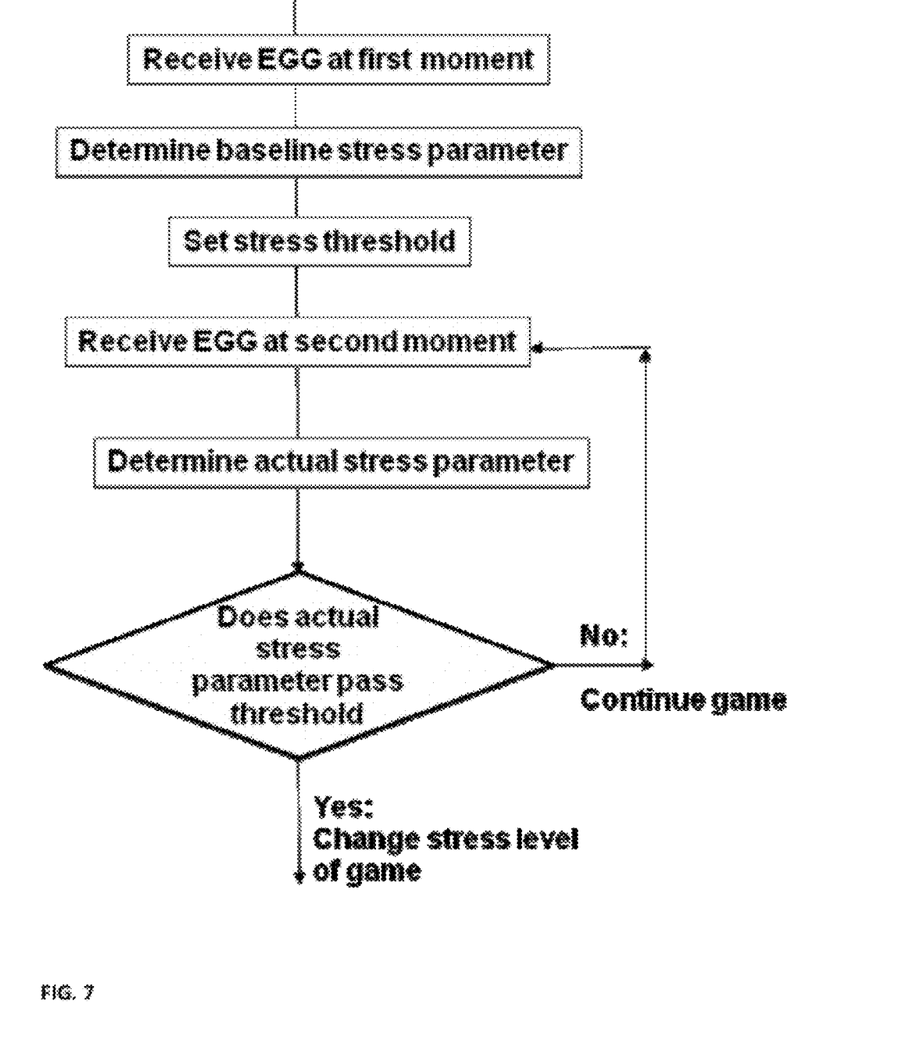

FIG. 7 illustrates steps related to measuring the stress parameter at a first and a second moment or period and related game stress level.

In yet a further embodiment, when the actual stress level does not increase, the computer 8 may decide to make the game more stressful, so to increase the patient's tolerance to pain.

As described and shown above, a smell generator can be connected to the computer wherein the computer can selectively and interactively cause one of a plurality of odors to be generated near the patient, in response to events occurring in the therapeutic videogame; a plurality of smells that can excite or relax the patient, as needed (determined by input from the neural headset).

Also as described and shown above, a 3D sound system can be connected to the computer wherein the computer can selectively cause one of a plurality of directional sounds to be generated near the patient in response to the events happening in the therapeutic videogame; computer alters intensity of sound, as well as type of sound and pitch in response to input from the neural headset.

Further as described and shown above, a temperature control system connected to the computer wherein the computer can selectively cause the patient to sense varying temperatures, so to immerse the patients into the simulation and to reduce the level of stress and pain based on input from the neural headset.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

We claim:

1. A system for treating pain in a patient, comprising:
   a computer;
   a rehabilitation table that can be tilted and lifted/lowered under control of the computer;
   a display that can display to the patient a plurality of therapeutic videogames under control of the computer, the therapeutic videogames having a physical and cognitive difficulty level associated with movements and a scene shown in the therapeutic videogame;
   one or more bio-sensors, including a neural headset, configured to be worn by the patient and connected to the computer to provide one or more inputs to the computer; wherein the computer analyzes the one or more inputs to the computer from the one or more bio-sensors and controls the difficulty level associated with the physical movements and cognitive problems shown in the therapeutic videogame in accordance with the inputs and a baseline parameter of an electroencephalography (EEG) signal obtained before treatment;
   a smell generator connected to the computer wherein the computer can selectively and interactively cause one of a plurality of smells to be generated near the patient, in response to events occurring in the therapeutic videogame; wherein the plurality of smells can excite or relax the patient, as needed as determined by input from the neural headset;

a 3D sound system connected to the computer wherein the computer can selectively cause one of a plurality of directional sounds to be generated near the patient in response to the events happening in the therapeutic videogame; wherein the computer alters the intensity of sound, as well as the type of sound and pitch in response to input from the neural headset; and a temperature control system connected to the computer wherein the computer can selectively cause the patient to sense varying temperatures, so as to immerse the patient into a simulation and to reduce the patient's level of stress and pain based on input from the neural headset.

2. The system of claim 1, wherein the computer alters table tilt based on the outputs of the one or more bio-sensors.

* * * * *